United States Patent
Mallon et al.

[19]

[11] Patent Number: 5,954,206
[45] Date of Patent: Sep. 21, 1999

[54] OPTICAL INSPECTION SYSTEM

[75] Inventors: John Mallon, County Limerick; Maurice Moynihan, Dublin, both of Ireland

[73] Assignee: Oseney Limited, Ireland

[21] Appl. No.: 08/765,842

[22] PCT Filed: Jul. 25, 1995

[86] PCT No.: PCT/IE95/00038

§ 371 Date: Jun. 20, 1997

§ 102(e) Date: Jun. 20, 1997

[87] PCT Pub. No.: WO96/03226

PCT Pub. Date: Feb. 8, 1996

[51] Int. Cl.[6] .................................................. B03B 5/24
[52] U.S. Cl. ...................... 209/580; 209/587; 209/639
[58] Field of Search ........................... 209/577, 580–582, 209/587, 639

[56] References Cited

U.S. PATENT DOCUMENTS

| | | | |
|---|---|---|---|
| 4,146,135 | 3/1979 | Sarkar et al. | 209/580 |
| 4,147,619 | 4/1979 | Wassmer et al. | 209/565 |
| 4,225,242 | 9/1980 | Lane | 356/407 |
| 4,558,786 | 12/1985 | Lane | 209/558 |
| 4,630,736 | 12/1986 | Maughan et al. | 209/581 X |
| 4,699,273 | 10/1987 | Suggi-Liverani et al. | 209/580 |
| 5,652,432 | 7/1997 | Yaginuma et al. | 209/580 X |

FOREIGN PATENT DOCUMENTS

| | | |
|---|---|---|
| A 27 23 674 | 12/1977 | Germany . |
| 1520858 | 8/1978 | United Kingdom ................... 209/580 |
| 2 060 166 | 9/1990 | United Kingdom . |
| WOA9414053 | 6/1994 | WIPO . |

*Primary Examiner*—Boris Milef
*Attorney, Agent, or Firm*—Rossi & Associates

[57] ABSTRACT

An optical inspection system inspect products passed through an inspection region. Light is directed onto the products form optical control units including light emitting diodes. Light emitted from the diodes is directed by cylindrical lenses onto the products at a specified target region, and a sensor detects light reflected from the products. Focussing is achieved by an outer row of the diodes being displaced outwardly relative to axes of respectively cylindrical lenses, so that light originating from the outer rows of diodes converges towards that passing along a central axis extending from a central row of the diodes through a central lens to the target region, light from all rows of the diodes being therefore focussed substantially at the target region.

19 Claims, 10 Drawing Sheets

OPTICAL INSPECTION SYSTEM

This invention relates to optical inspection systems and/or sorting systems. The invention is especially directed to optical inspection systems for use in the control of fruit or vegetable sorting systems and harvesters, in packing houses or in canning factories.

Systems of this kind are used to inspect typically the ripeness of the fruit or vegetable and/or the presence of dirt clods or other foreign materials and/or the presence of colour defects and to establish criteria for separating good product from defective product or other unwanted matter.

Specific examples are checking the ripeness of tomatoes or fruit. In a known system, light incident upon tomatoes is reflected and the reflected light monitored to establish the degree of ripeness of the product and/or the presence of dirt and/or product defects. In particular arrangements, light emitting diodes, LEDs, are used, to direct light onto product typically falling past the light sources. A number of disadvantages are however apparent in existing systems of this kind, in particular associated with build-up of dirt on windows through which the light is usually directed and behind which the light sources and also the light sensors are located.

A further problem is adherence of product portions or other extraneous material to whatever feature defines the rear boundary of the target region, typically a curtain, as such unwanted matter or dirt may reflect light back thereby giving spurious indications. A still further problem arising out of illuminating an inspection zone or region with LEDs is that the illumination across the inspection region may be patchy or non-uniform, which leads to non-uniform inspection sensitivity.

It is an object of the invention to provide an optical-light product inspection system overcoming at least in part certain of the disadvantages identified above.

According to the invention, there is provided an optical inspection system for edible natural products comprising an inspection region through which said products pass, means for directing light onto said products during their passage through said inspection region, and means for detecting light returned from said products, wherein said means for directing light onto the products comprises an optical system for focussing light substantially at a specified target region within said inspection region.

The system of the invention may comprise a plurality of said light directing means, in particular two said light directing means.

The or each light directing means suitably comprises a multiplicity of light emitting sources and a lens system for focussing light emanating from said sources substantially at said target region. Preferably, said multiplicity of light emitting sources comprises a first multiplicity of said sources for emitting light of at least one first wavelength and at least one further multiplicity of said sources for emitting light of at least one second wavelength, said at least one first wavelength and said at least one second wavelength being selected in dependence on optical characteristics of the products to be inspected, and the number of said first multiplicity of said sources of said at least one first wavelength may be balanced against or matched to the number of said further multiplicity of said sources of said at least one second wavelength, so that substantially similar processing may be applied to signals provided by said returned light detecting means substantially independently of the wavelength of the returned light. Said at least one second wavelength is suitably different from said at least one first wavelength, but where a multiplicity of first and second wavelengths are used, so that the first multiplicity of sources includes sources of a variety of wavelengths as also does the second multiplicity, then at least some of the second wavelengths may be the same as some of the first wavelengths. Thus partial overlap of wavelengths may exist in certain circumstances.

In a favoured embodiment of the system of the invention, said light emitting sources are arranged in a plurality of substantially parallel rows and said lens system comprises a plurality of substantially cylindrical lens portions extending generally parallel to said rows of said sources, a respective said lens portion corresponding to each of said plurality of rows. Said lens system may be a compound lens system, for example, comprising a unitary structure, which may be extruded or machined from solid.

In an especially preferred embodiment, at least one of said rows of light emitting sources is suitably laterally displaced relative to the longitudinal axis of the respective lens portion, the or each light directing means comprising a multiplicity of rows of said light emitting sources.

In a particular construction, the or each light directing means comprises at least three rows of light emitting sources, a central row of said sources for emitting light of at least one first wavelength being flanked by at least two rows of said sources for emitting light of at least one second wavelength, said at least one second wavelength being different from said at least one first wavelength, and at least one row of said sources of said at least one second wavelength being located to each side of said central row.

In one such arrangement, the or each light directing means may comprise three rows of said light emitting sources, a central row of red and/or infrared said sources being flanked by two rows of green said sources, one to each side of said central row.

In any variant of the system of the invention, each said light emitting source may comprise a light emitting diode.

The system suitably also comprises means for controlling product movement through said inspection zone so that said products pass substantially through said target region, for example including a product conveyor cooperating with product guide arrangements, product diverter arrangements, and inspection region enclosure arrangements.

Said means for detecting returned light is preferably located in substantial proximity to said light directing means, such as substantially centrally between two said light directing means.

Said light directing means and said returned light detecting means are preferably separated from said inspection zone by light-transmitting but product-impermeable means, such as a window.

The or each said light directing means is suitably disposed so that the spacing between said target region and said light-transmitting but product-impermeable means is sufficient to substantially minimise build-up of unwanted matter on a surface of said light-transmitting but product-impermeable means directed towards said target region.

In a system according to the invention, said returned light detecting means suitably comprises at least one sensor responsive to reflected light received from products passing through said target region. In a particular construction of the invention, the system comprises a multiplicity of said sensors disposed in a substantially linear array.

The system may also comprise means for substantially enclosing said inspection region against unwanted ejection of products or other matter. Said enclosing means may substantially define an enclosure for said inspection region, and may include, at the opposite end or side of said inspection region from the window and inspection features in a single-sided installation, a curtain or other like wall portion for closing off the inspection zone.

In a system according to the invention, associated light directing means and returned light detecting means may define a substantially single optic unit located to one side of said inspection region. Alternatively, the system may comprise a plurality of associated light directing means and returned light detecting means defining a plurality of optic units, each of which includes at least one light directing means and at least one returned light detecting means, said plurality of optic units being located substantially equidistantly from one another around said inspection region. Thus in this variant of the invention, the optic units are spaced substantially symmetrically about the inspection region, as viewed from the direction of advance of the product. Three such units may therefore be spaced at 120° from one another, while in a preferred embodiment of this variant of the invention comprising two said optic units located substantially diametrically opposite one another on opposite sides of said inspection region, the units are spaced by 180°.

A system according to the invention may further comprise (a) means for advancing products to said inspection region, for example, a conveyor, (b) means for deriving at least one signal indicative of at least one specified characteristic of the products by analysis of light returned from said products, and (c) means for effecting an operational output on the basis on said at least one signal. Said means for effecting an operational output may provide at least a signal for driving deflector means for separating rejected products from accepted products, and/or information for compilation of product quality statistics.

The invention also extends to an optical inspection system substantially as described herein with reference to and as shown in the accompanying drawings, as well as to sorting systems comprising inspection systems according to the invention.

Embodiments of the invention are now described having regard to the accompanying drawings, of which

Figure 1:
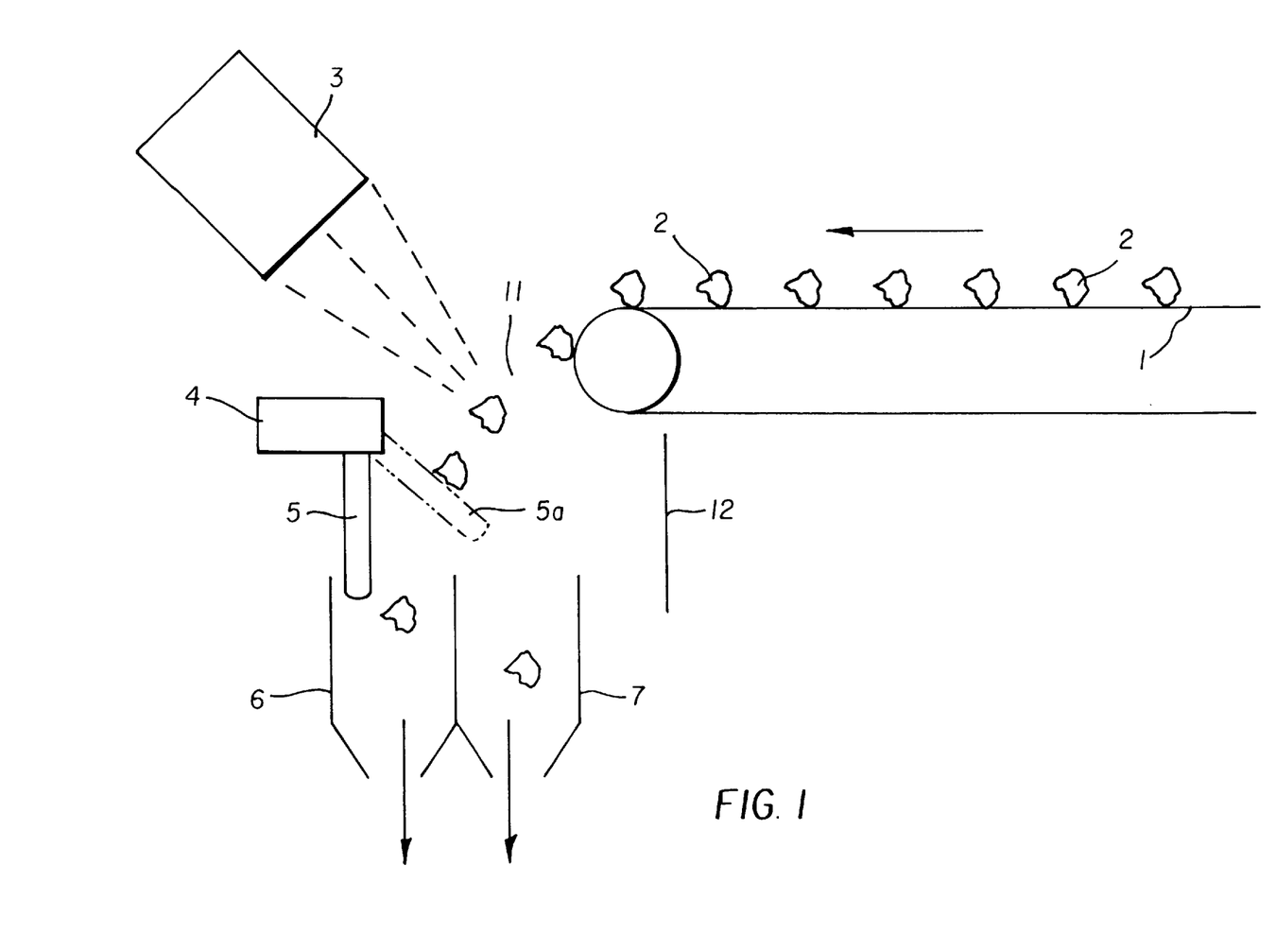
FIG. 1 is a diagrammatic representation of a fruit or vegetable sorting apparatus according to the invention.

An embodiment of fruit or vegetable sorting apparatus of the kind in which the invention may be applied will now be described as a whole, having regard to FIG. 1, this embodiment being particularly applicable to a system according to the invention for use in an outdoor or field situation. As shown in FIG. 1, a flat belt conveyor 1 advances product 2 to be monitored and inspected to an inspection station, where it falls from the end of the belt through an inspection zone 11. At the inspection station, an optical inspection device 3 is mounted at a spacing from the end of the flat feed conveyor 1 and on the opposite side of the inspection zone 11 from the conveyor end, to monitor product passing through the inspection zone 11. Zone 11 is closed off at the rear, i.e. the boundary of zone 11 remote from device 3, by a curtain 12. This boundary defined by a curtain 12 is located below the end of conveyor 1 at which the product falls through the inspection zone. The purpose of the curtain is to prevent product or waste matter, such as stones or the like, from being thrown out of the operating region of the machine and possibly injuring an operator or other party in the vicinity of the unit. The action of the various operating mechanisms in this region of the system may result in relatively random and high energy displacements of portions of product or waste material, and it is accordingly necessary to ensure protection against the unwanted ejection of material out of this region. The curtain 12 and other enclosing arrangements fulfill this function. Also mounted at the same end of the conveyor but below the inspection 11 is a reject mechanism 4. The inspection zone 11, device 3 and reject mechanism 4 are substantially the same width as the belt. Both the inspection device 3 and the reject mechanism 4 thus extend transversely across the entire path of advance of product 2 on belt 1, so that all product conveyed forwards by the belt may be monitored, inspected, and accepted or rejected as appropriate.

Product 2 dropping off the end of the belt 1 passes through inspection zone 11 and then passes in proximity to a product deflector mechanism defined by a bank of movable fingers 5, which provide the operating elements of the reject mechanism 4. The fingers 5 have a "normally open" disposition to allow good product to fall directly into a bin 6 for acceptable product, as shown in solid outline in FIG. 1. During the freefall period after the product leaves the conveyor but before it reaches the fingers, the falling product 2 is inspected by the monitoring features of the inspection device 1. If a particular individual product is defective or a particular item inspected is to be rejected, a signal is sent from device 3 to the rejector 4 which activates the relevant fingers 5 to deflect or "kick" the defective product or extraneous material to be removed from the product stream into a discharge arrangement by pivoting selected members of the finger bank corresponding to the position of the unwanted item into an activated disposition shown in dotted outline in FIG. 1, reference 5a. Reference 6 denotes the bin or reception arrangement for good product for further advance, into which good product 2 falls past fingers 5 in their normal or clear operating disposition. Reference 7 denotes a bin or path of advance or collection facility for reject product, into which defective product is deflected or kicked by virtue of fingers 5 being rotated upwardly and to the right as shown in FIG. 1. Thus in the arrangement shown in FIG. 1, in the normal disposition of the fingers, they fulfill no deflecting function and the good product continues its freefall path of movement into the bin or receptor 6. Depending on the balance between good and reject product in any particular product flow, a converse arrangement may however alternatively be provided, in which the fingers occupy a normally deflecting disposition, so that the majority of product is deflected into a reject channel and the lesser proportion of good product is brought into a path for good or acceptable product by movement of the fingers into an open configuration. The inspection device of the invention may be adapted to detect defective product and/or the presence of extraneous matter. In the case of fruit or vegetable products, defective product may include unripe or overripe product, while extraneous matter may include earth, leaves and other unwanted vegetable material.

In a system of the foregoing kind, a variety of sensing arrangements may be applied in device 3. The present invention is directed to systems in which optical detection arrangements are applied, and in particular optical-light sensors such as light-emitting diodes, LEDs, which direct light onto the product to be monitored. The inspection device then also includes sensors responsive to light reflected from the product to provide the required appraisal or assessment of product condition.

Unit 3 thus suitably comprises a closed housing accommodating LEDs or other light sources, together with cooperating light sensors, all located behind a protective window or other light-transmitting but product-impermeable arrangement through which light is directed from the LEDs into the inspection zone 11, and through which also reflected light from monitored product returns to be picked up by the detecting or light-responsive sensors. At the opposite end of zone 11 from the window of unit 3, the inspection region is closed off by the curtain 12 or other like closure feature and is also further enclosed by other wall portions for the purpose described above, namely prevention of ejection of product or waste matter.

Figure 2:
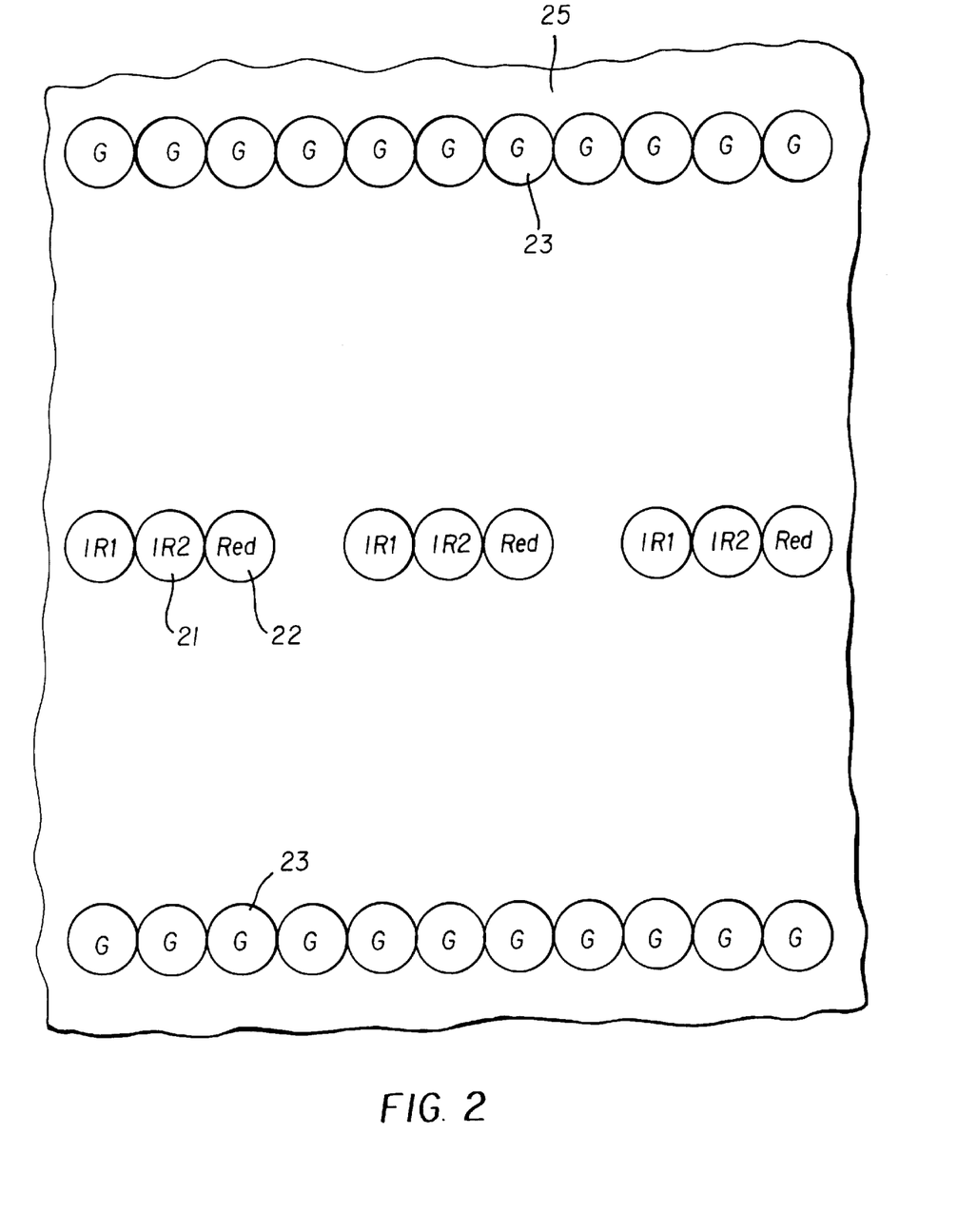
FIG. 2 is a representational front view of a circuit board portion mounting a number of light emitting diodes for use in the optical inspection system of FIG. 1.

Referring now to FIG. 2, which is directed to particular features of the present invention, three rows of LEDs are provided, a central row of infrared 21 and red 22 light sources, in partially alternating array, each red being spaced from adjacent red LEDs by two infrareds, and a row of green LEDs 23 to each side of the central row of red/infrared, each green row extending generally parallel to the central red/infrared row. Suitably, there are four LEDs for each 25.4 mm (1 inch) of linear length of each row, and a suitable dimension for row separation is 28.5 mm. These dimensions are however exemplary only. Suitably the LEDs are mounted on a circuit board portion designated by reference 25.

Figure 3:
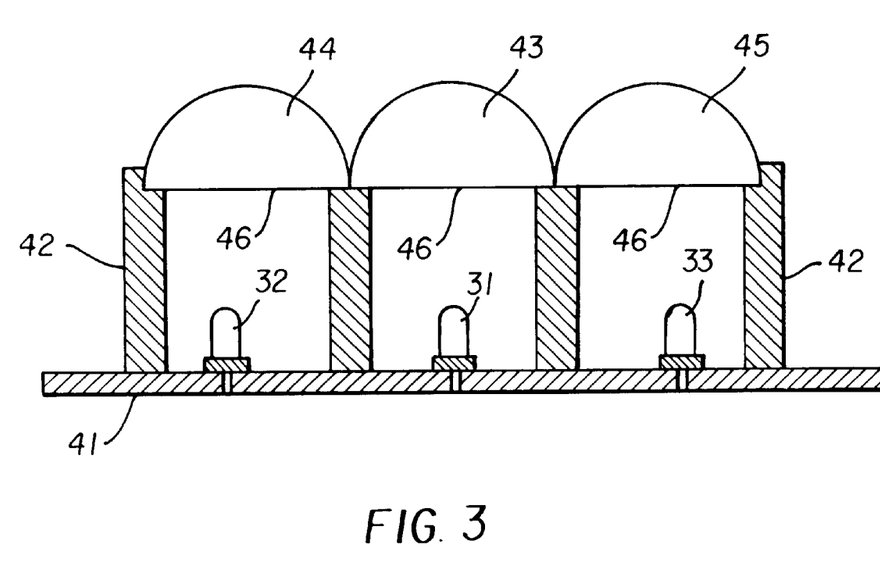
FIG. 3 is a generally diagrammatic cross-section viewed from the lefthand side of FIG. 2 of the LED mounting arrangement of the system of the invention.

These rows, now identified as row 31, red/infrared, and 32, 33, green, are shown in end view in the end sectional depiction of FIG. 3. This drawing shows the illumination assembly. The LEDs 21, 22, 23 of FIG. 2 are mounted on a single underlying printed circuit board 41, a portion 25 of which is shown in FIG. 2, and each row 31, 32, 33 of LEDs mounted on this single circuit board is separated from each adjacent row by means of longitudinal lens supports 42. Longitudinal lens structures 43, 44, 45 extending along the length of each row 31, 32, 33 are placed above and at a spacing from the LEDs 21, 22, 23. Each lens 43, 44, 45 consists of a half-round or semi-cylindrical structure, extending in the representation of the drawing perpendicular to the plane of the paper, the half-round bars 43, 44, 45 being in edge contact with one another along the sides where the flat faces 46 meet their curved faces.

The central row 31 of LEDs, namely the red/infrared row, is aligned along the optical axis of the lens 43 above it. In other words, this central row 31 of LEDs 21, 22 is itself centrally aligned with the axis of the central lens 43. The green rows 32, 33 to each side of the central row 31 are however in each case physically offset from the axis of their respective lens 44, 45, but all three rows 31, 32, 33 are mounted in or on the same plane, namely the plane of the printed circuit board 41. The flat faces 46 of the cylindrical lenses 43, 44, 45 extend parallel to this plane. This physical offset of the outer rows 32, 33 of LEDs 23 from the axes of their respective lenses 44, 45 is such that all three rows 31, 32, 33 of LEDs focus on a single target region. The outer rows 32, 33 use the refractive properties of their respective lenses 44, 45 to focus at a target region to which light from the central row 31 is also directed along the central axis of the lens 43. Thus as shown in FIG. 3, the offset of row 32 is to the left, i.e. outwards from the central longitudinal axis of lens 44 relative to the middle red/infrared row 31, while that of row 33 is to the right, i.e. again outwards from the axis of lens 45 relative to the middle row 31 and its lenses 43. In physical terms, each row 32, 33 is shifted laterally or sideways to be outward of the longitudinal central axis of the respective lens portions 44, 45 relative to an axial central plane of the assembly, i.e. that defined by central row 34 and the longitudinal axis of lens 43, which are parallel.

Further features of the illumination assembly as shown in FIG. 3 are that no lens supports are positioned across the assembly, as such an arrangement would interrupt light continuity. Only the longitudinal supports 42 are provided. The LEDs are mounted on the single printed circuit board 41, and suitably underlie the lens structure by some 30 mm, this being the spacing between the flat faces 46 of the lenses and the upper planar surface of the printed circuit board 41. The lenses 43, 44 and 45 are suitably half round bars of 25.4 mm diameter, namely 1 inch.

Figure 4:
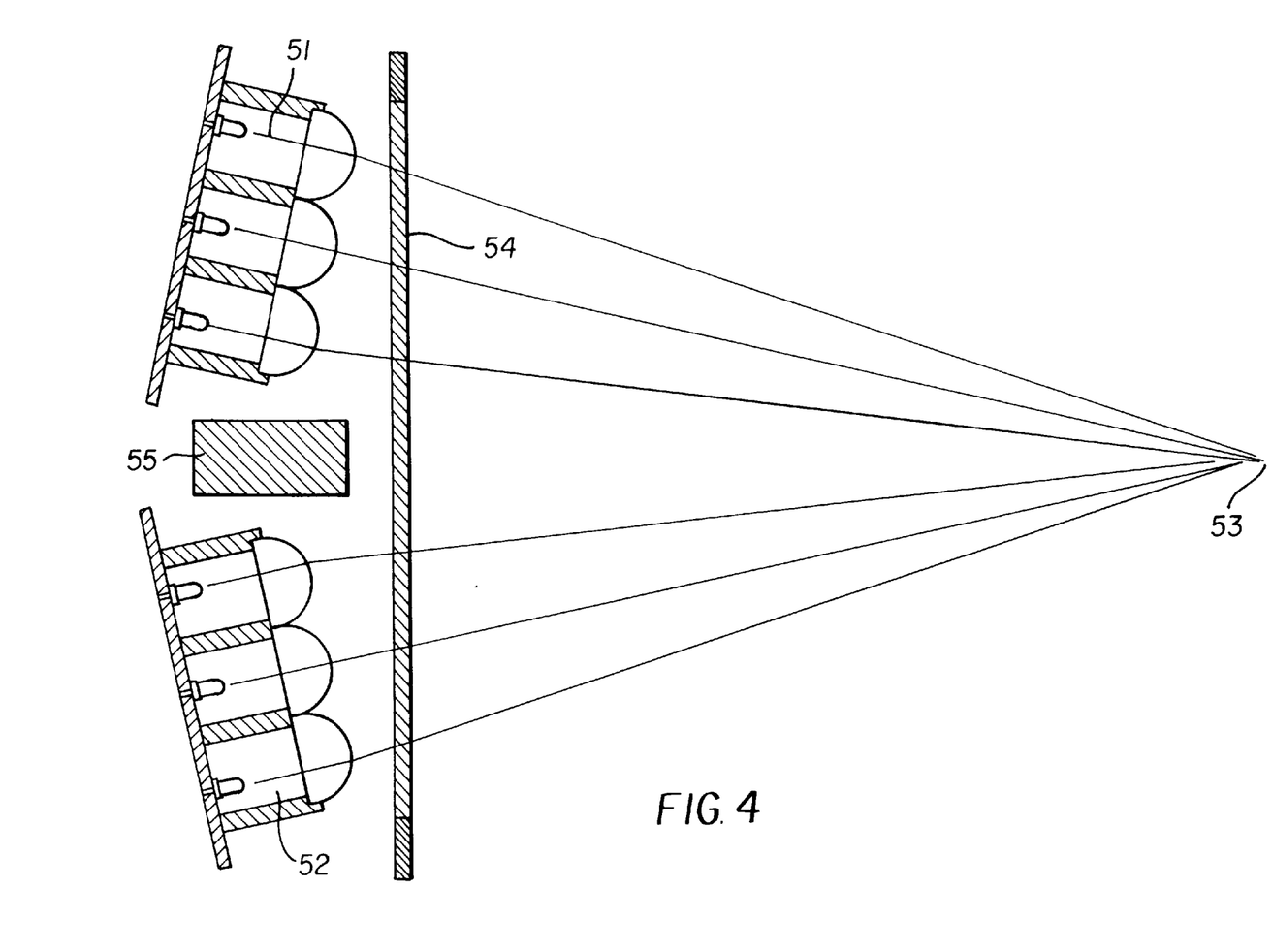
FIG. 4 is a generally diagrammatic assembly drawing showing a manner of mounting the LED circuit boards in a practical optical inspection system according to the invention.

The practical advantages of this arrangement are shown in the assembly drawing of FIG. 4. Two lens/LED arrays 51, 52 in accordance with FIG. 3 are shown, each of which focuses on or at a single target region 53 located at an appropriate spacing from the window 54 which protects the LED assemblies 51, 52 and the detector assembly or assemblies denoted generally by reference 55 from the falling product and dirt. The two LED assemblies 51, 52 focus on this single target region 53. The assemblies 51, 52, 55 are thus located behind the window 54. An advantage achieved by this focussing system is that the target region 53 past or through which the fruit or other product travels in freefall may be located at a substantially greater distance from the window 54 than is the case for known unfocussed systems. A significantly shorter spacing between light source and inspection region is required in the absence of LED focussing in order to attain the required density of light in the inspection region. With such abbreviated spacing, the problem of dirt build-up on the window becomes significant. When the inspection region is close to the window, product travels in relatively close proximity to the window, to such extent that there is accelerated transfer of dirt and other unwanted matter onto the window, such as by product bouncing against the window, spattering, or other action inevitably associated with the passage of the product through the inspection region. By virtue of the extended spacing of the system of the present invention, dirt build-up on the window from product passing through the inspection region, which is a particular feature of known systems, is reduced or substantially avoided. Spacing between the assemblies 51, 52 at their inner edges is suitably approximately 50 mm (2 inches), the detector assembly 55 being accommodated in this region. The detector arrangement comprises a multiplicity of sensor units disposed in an elongate linear array extending parallel to the rows of LEDs of the arrays 51, 52.

A very particular advantage of the invention is therefore that it facilitates especially greatly improved cleanliness of the protective window behind which the light assemblies are located. Thus a particular structural feature of the arrangement is that the target zone is selected to be located sufficiently far from the protective window as to substantially eliminate any significant build-up of dirt on the window during operation of the system. In the particular installations described, this results in the dimensions quoted, but the system is not limited to such specific dimensions, the criterion being that the spacing should be sufficient as to minimise dirt build-up, and this distance may vary depending on the nature of the product as well as structural parameters. Relatively hard product may be handled satisfactorily with a lesser spacing between the target zone and the window, while soft product prone to possible splattering may require a greater spacing.

The invention also offers a further advantage in regard to the curtain or flap or screen 12 behind the target region 53 (FIGS. 1 and 4). Product bouncing off this curtain or flap 12, or bumping against it, may become adhered in part to the curtain 12, or extraneous matter may become detached from the product and adhere to the curtain 12. In systems in which the light from the LEDs is not focussed at any specific target location, some of the light incident on the curtain may then be reflected back by virtue of the presence of this unwanted material to be detected by the sensor, and spurious output signals thus result. In the system of the invention, light is focussed at a more specific target region, and thus substantially only light reflected back from this region is picked up by the detectors. Accordingly the possibility of the system responding to light reflected back from the curtain or from extraneous matter which has built up on the curtain, is largely obviated, since the system is not focussed on the curtain. The level of spurious signals may accordingly be reduced, or such signals may be substantially eliminated. A further advantage of the system over previous arrangements making use of LEDs for illuminating an inspection region is that according to the invention, the number of LEDs used is reduced or cut down, but the uniformity and intensity of illumination in the region of interest, i.e. the target region of the inspection zone, is increased.

A further very significant advantage of the invention is accordingly that because of the use of focussed light and because also of the improved cleanliness of the window, it is possible to use a very much lesser number of LEDs than applies to installations using non-focussed light. The number of LEDs may be reduced by a factor of up to 5 and in some instances 10, as compared with non-focussed arrangements.

In the system of the invention, the inspection zone 11 is preferably laid out so that product falling from the conveyor belt 1 will for the most part pass through the target region 53. Further guide arrangements or control features may also be put in place to ensure appropriate placement of product within the inspection zone for proper monitoring to take place, i.e. to ensure positioning of product at the target location or in substantially the target region, for incidence of the focussed light inspection beams on the passing product.

Figure 5:
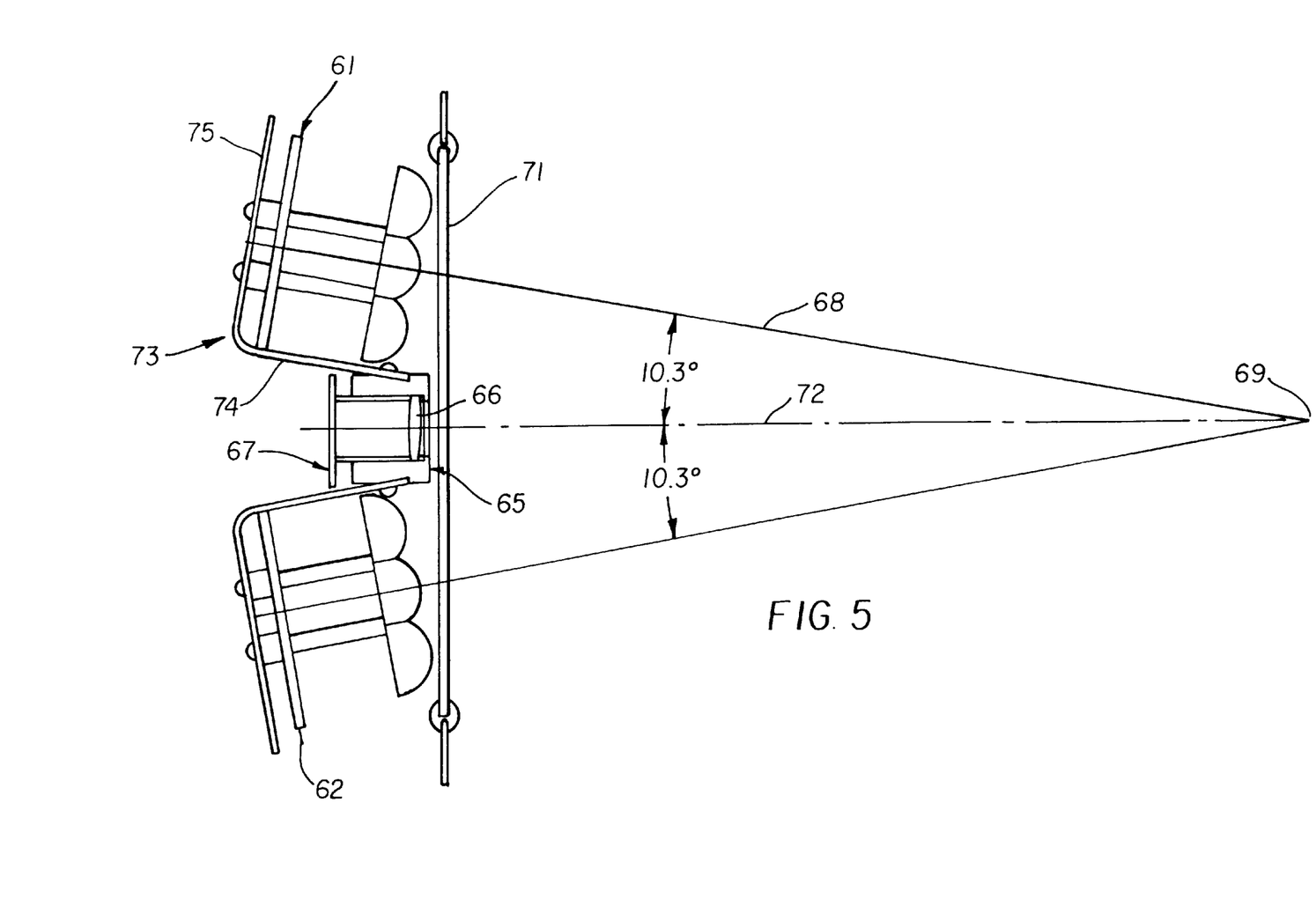
FIG. 5 is a further assembly drawing showing in greater detail than FIG. 4, a manner of mounting the LED circuit boards in a practical optical inspection system according to the invention, before the fitting of the LEDs themselves.
Figure 6:
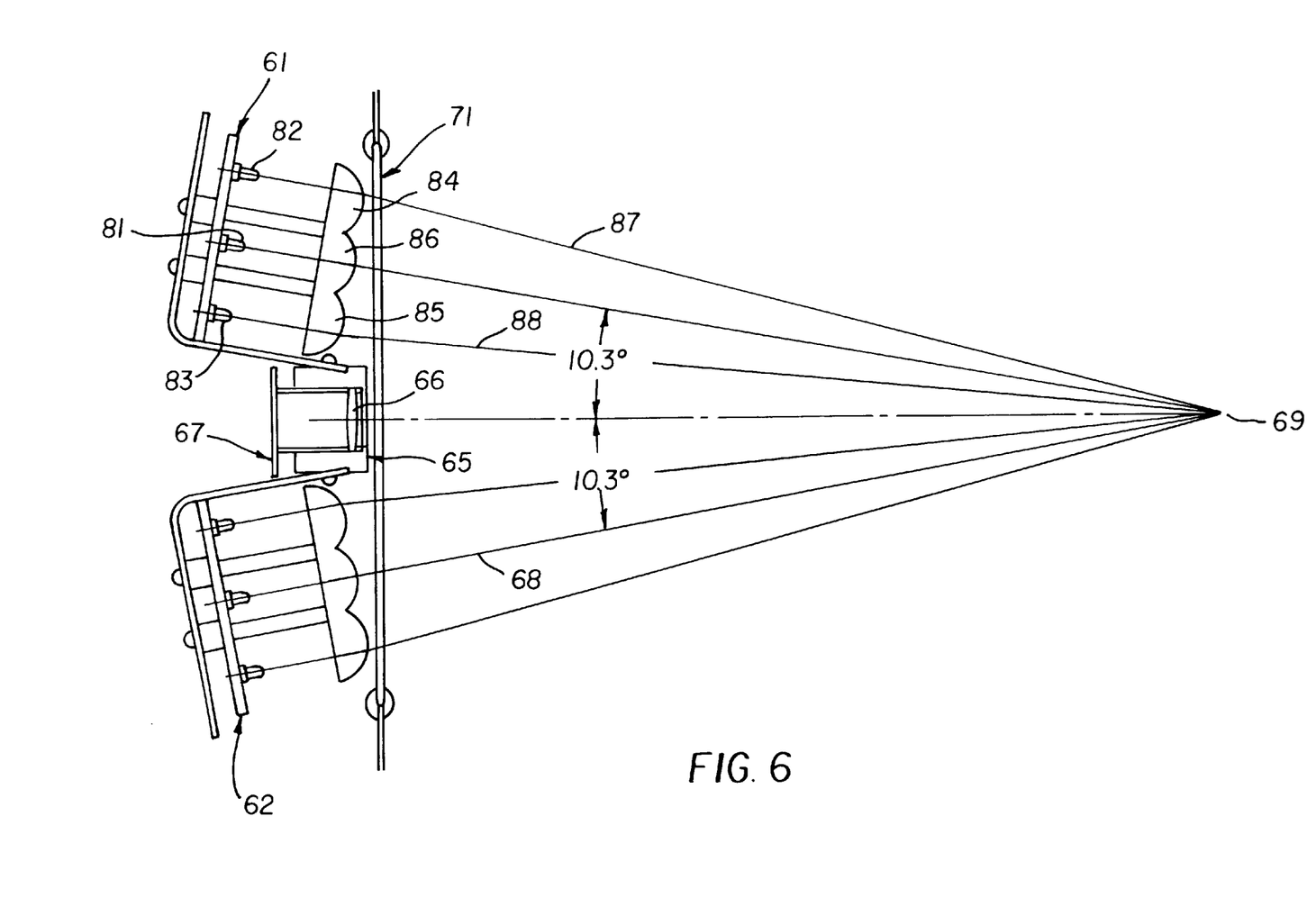
FIG. 6 is the assembly drawing of FIG. 5 following fitting of the LEDs to the structure.

In the practical assembly shown in FIGS. 5 and 6, referring first to FIG. 5, the LED assemblies 61, 62 are mounted one to each side of a central optic bar 65 which accommodates an elongate array of lens structures 66 for focussing reflected light on a detector board 67. Each sensor unit 66, 67 mounted in elongate axial array on the optic bar between the LED units may also be provided with arrangements for enhancing sensor performance so that each sensor monitors a particular axial sector of the target zone in optional manner and the effect of internal reflections may be minimised. The construction of each LED assembly is as previously described. The central optical axes 68 of the assemblies 61, 62 are aligned to focus on a target region 69 some 290 mm (11.5 inches) from the window 71 behind which the LED assemblies 61, 62 and the detector system 66, 67 are housed. The optic axes 68 of the assemblies 61, 62 thus each subtend an angle of some 10.3 degrees with the axis 72 of the central optic bar/detector unit 65. The included angle between the two optical axes 68 of the respective LED assemblies 61, 62 is thus approximately 20.6 degrees.

In the arrangement shown, this angled alignment of the assemblies 61, 62 is suitably achieved by each assembly 61, 62 being supported on an angled mounting bar 73 of generally L-shaped configuration, one limb 74 of which is secured to an appropriately sloping or bevelled side surface of the optic bar 65. The second right-angled limb 75 then extends outwardly at an angle such that a direction normal to it is aligned with or parallel to the LED assembly axis 68. Bars 73 and 65 have an elongate dimension in a direction generally perpendicular to the plane of the drawings, FIGS. 5 and 6.

In FIG. 6, the system of FIG. 5 is shown with the LEDs 81, 82, 83 fixed in position, and the manner in which the outer LEDs focus on the target region 69 on which the overall optical axis 68 of each assembly 61, 62 is aligned is also shown. As previously described, each outer LED row 82, 83 is offset relative to the central axis of its respective lens 84, 85, so that the light path from the LEDs 82, 83 is also focussed at the target region substantially along paths designated by references 87 and 88. LED spacing from the lens structures is approximately 33 mm, 1.3 inches, all of the dimensions being however exemplary only.

It will be appreciated that the light paths 87 and 88 and the other light paths from the outer LED structures are indicated in only highly diagrammatic manner, as the optical effect of LED offset relative to the cylindrical lens is not readily clearly depicted in simplified manner but is nonetheless wellknown from optical principles. Thus the representation of the light paths shown in the drawings and in particular in FIGS. 4 and 6 is representational only in this respect and is set down for clarity of description of the invention and does not necessarily indicate a precise light path in an actual physical structure. It will also be further appreciated that the target zone or region 53 is not necessarily a point or line location such as is indicated in the various diagrammatic representations of the drawings, but rather that the target region typically extends axially over a distance along the central axis 72 of the overall structure which is defined or determined by the tolerances of the assembly. Similarly, the target region or zone has a dimension transverse to the central axis 72 again dependent on the precision with which the various lens structures are aligned. Thus the target region or zone essentially consists of a three-dimensional region of complex configuration extending generally transversely across the inspection zone to form a notional target line, depicted as an idealised target point in the side views of FIGS. 4, 5 and 6. The term "target region" or "target zone" is thus to be understood in this context and does not necessarily refer to a point or line location in any practical installation.

According to a variant of the invention, it is possible to use cylindrical lens arrangements in which the outer rows of LEDs are assembled without physical offset, but with the LED/lens assembly angled so as to focus the light onto the same target region as that for the central or optical axis row.

This arrangement requires however a greater number of circuit boards than the preferred arrangement shown in the drawings, but may be advantageous in certain circumstances. However, the arrangement of FIG. 5 provides for ease of pre-assembly of the sub-units of the system and precise aligned mounting of the LED/lens sub-assemblies on the optic bar 65.

The cylindrical lens assemblies may be made up by single compound lens structures, in which the three cylindrical lens portions 84, 85, 86 are parts or portions of a single extruded or moulded structure, or are machined from solid material to provide a single unitary lens structure, in preference to the three individual semi-cylindrical lenses already shown and discussed. Such an arrangement provides for simple and economical formation of the lens structures in question. It will however also be appreciated that the required lens structure may also be achieved by a succession of half-spherical or bullseye lenses arranged in an elongate array, but such an arrangement is not as structurally effective or economical as the simple semi-cylindrical arrangements described above, especially in the compound lens variation now particularised.

The numbers of each type of LED, type referring to the wavelength of output, may be selected so as to provide a generally equal signal response in the optical sensors when targeted on a surface of optical characteristics generally similar to those of the objects or produce to be inspected and sorted. This arrangement enables a single amplifier followed by an A-D converter to be dedicated to each sensor element, thereby eliminating any need to amplify the signal generated by each sensor to a different extent for each type of LED. Effectively, a balance is achieved by having more of the LEDs which produce a less bright level of light output.

In the foregoing detailed description, the colouration of the diodes has been referred to as red, infrared and green. The colouration of the diodes effectively depends on the wavelength of the light emanating from the diodes. The colourations already indicated are exemplary only and the invention is not limited solely to those colourations. Any suitable light wavelengths may be provided in the diode arrays in any suitable combination. For particular products, orange or yellow light may for example be favoured. Thus the requirement of the light sources is that they should be matched in wavelength to the particular optical requirements or characteristics of the product to be inspected. The invention is also not limited to the use of diodes only as the light sources, although devices of this kind represent a currently especially practical form of light source for the particular application.

The arrangement of the invention has also been described in terms of assemblies comprising three rows of diodes. Additional rows of diodes may however be provided and the respective arrays may for example consist of five or more rows. Such further variations may also be related to the colour characteristics required of the diode array by embodying light sources of differing wavelengths in a variety of combinations.

The system of the invention is especially advantageous in the sorting or treatment of tomatoes, in particular to establish ripeness and freedom from other defects. It may also be applied to the handling of other fruit or vegetable products. The system of the invention is also suitable for the detection of levels of defect and ripeness. Thus it is adapted not only to detect the presence of colour defects, but also whether a particular degree of colour defect merits rejection or not. Scars, black mould and other defects may also be similarly identified both as to their presence and severity. The system of the invention may further function as a size, in a size/grader combination. Thus the acceptance/rejection criteria of the system may also extend therefore to product size, optionally in combination with other product criteria.

Figure 7:
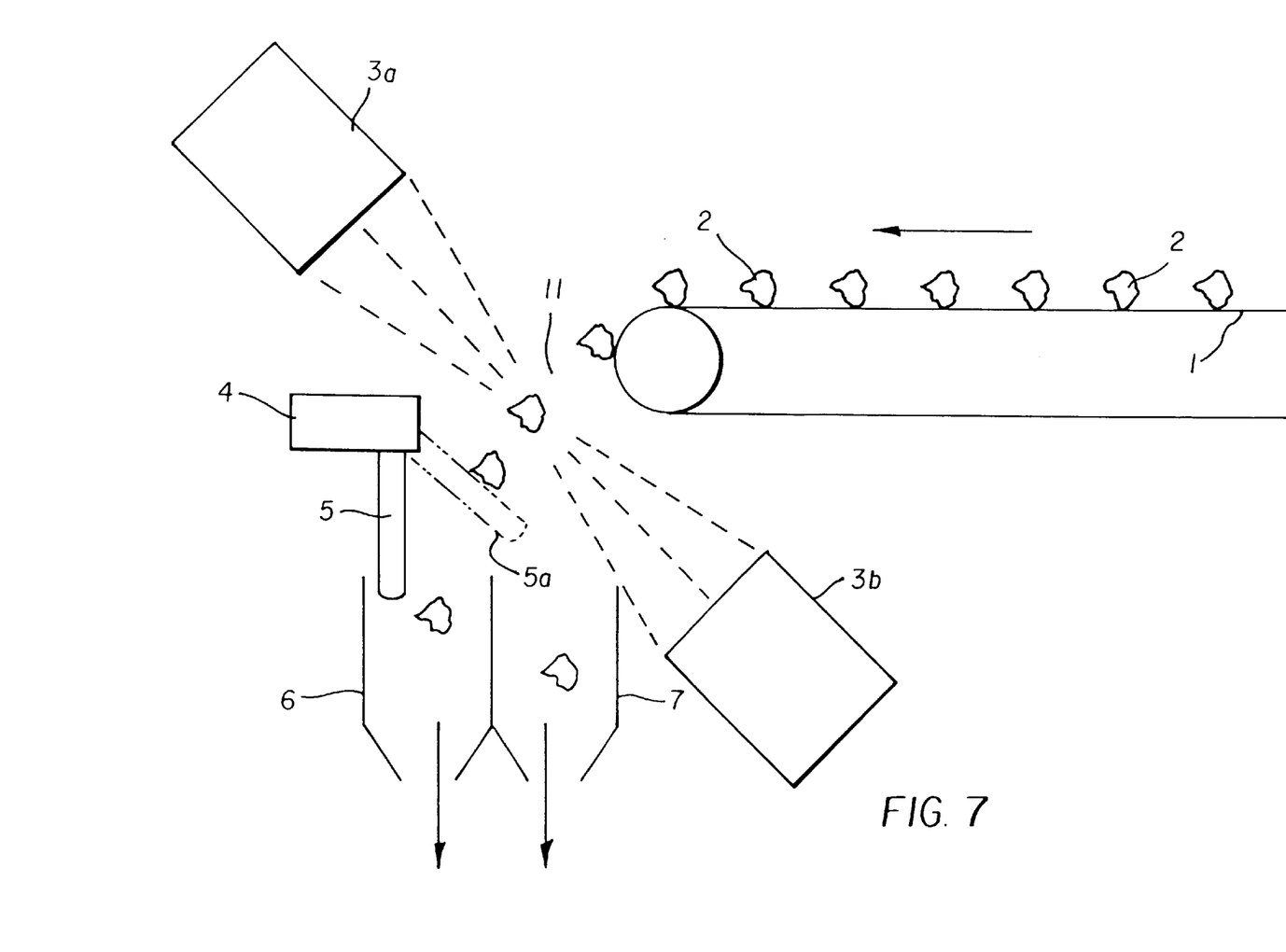
FIG. 7 is a diagrammatic representation similar to that of FIG. 1 showing an embodiment of the invention in which two optical inspection devices are applied.

FIG. 7 is a diagrammatic representation similar to that of FIG. 1, showing a system according to the invention in which two optical inspection devices 3a and 3b are provided, one located to each side of the inspection zone 11. Apparatus of this kind is suited to off-field operation and is typically used in a factory or processing environment. Differences from the arrangement of FIG. 1 are as follows:

The single inspection device 3 of FIG. 1 is replaced by two such devices 3a and 3b, and the curtain 12 is omitted. The inspection portion of the equipment is however similarly enclosed as in the arrangement of FIG. 1 to preclude violent expulsion of product or waste. Each optical inspection device 3a and 3b is similar to the construction already described and each device focusses onto the target zone or region 11 through which product 2 travels from the conveyor end. Because of this focussing, the opposed inspection units 3a and 3b function without interfering with one another, as each detector is individually responsive to light returned by product 2 within the target zone 11 only and is not affected by light from the respective opposed unit 3a or 3b located to the other side of the target region 11.

Figure 8:
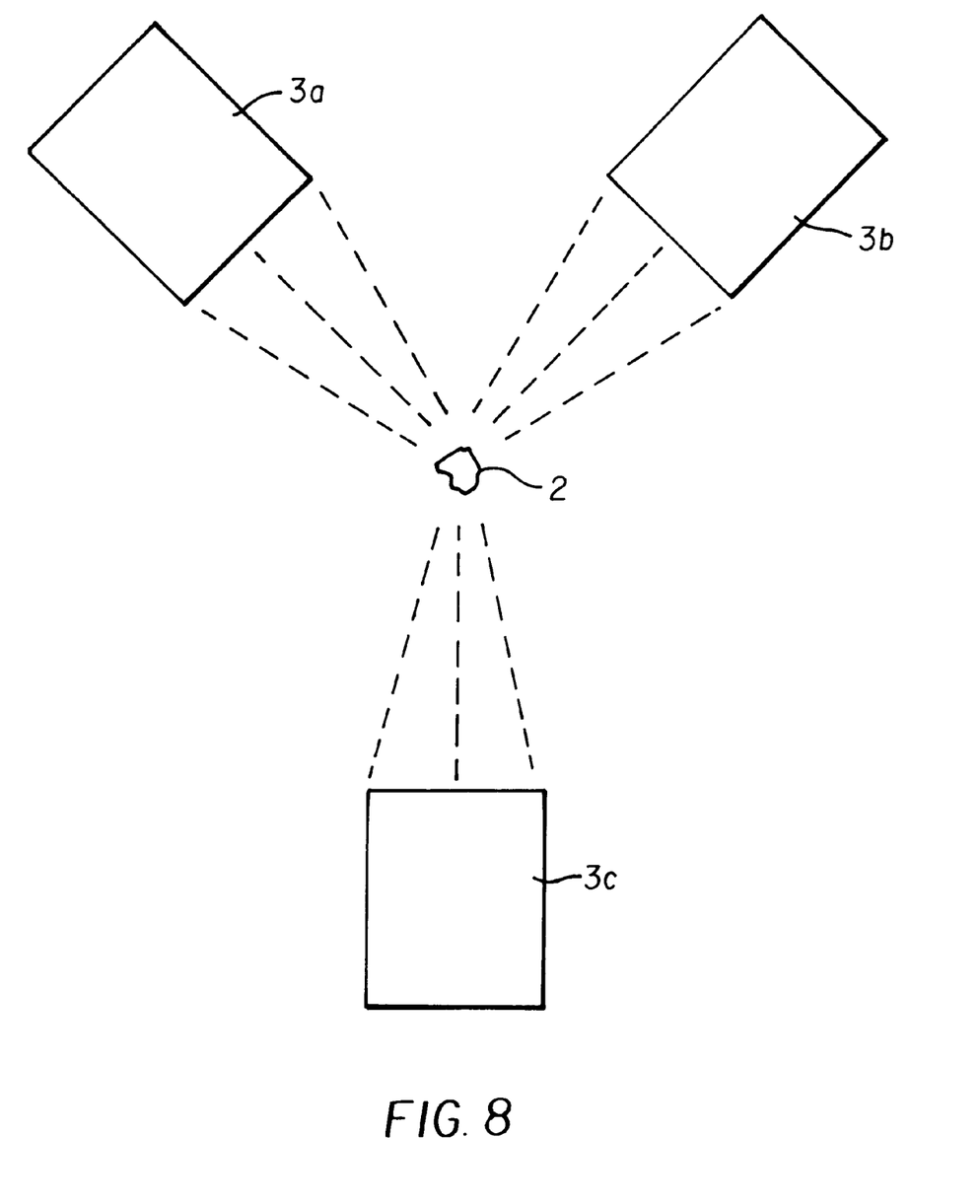
FIG. 8 is a highly diagrammatic top view of an inspection station at which three optical inspection devices in accordance with the invention are applied.

A system in accordance with the invention may also operate with three inspection devices 3a, 3b, 3c, as shown in the highly diagrammatic representational top view of FIG. 8. A product 2 is shown passing downwardly through the inspection zone 11, and three inspection devices 3a, 3b, 3c, located at respective angular spacings of 120° from one another, are positioned around this target zone, to again function in the manner already described.

Figure 9:
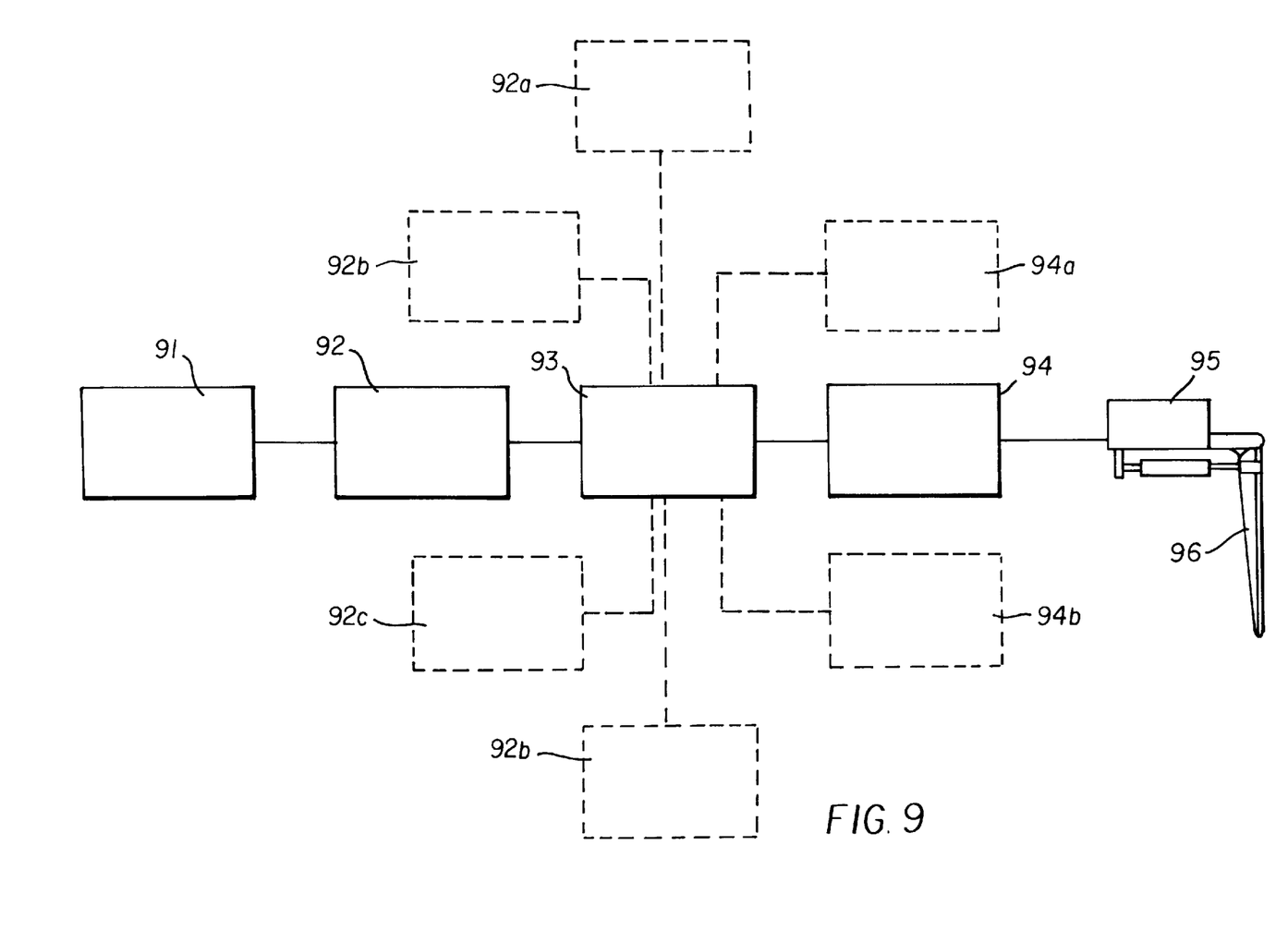
FIG. 9 is a block diagram for a sorting system of the invention such as is shown in FIG. 1.
Figure 10:
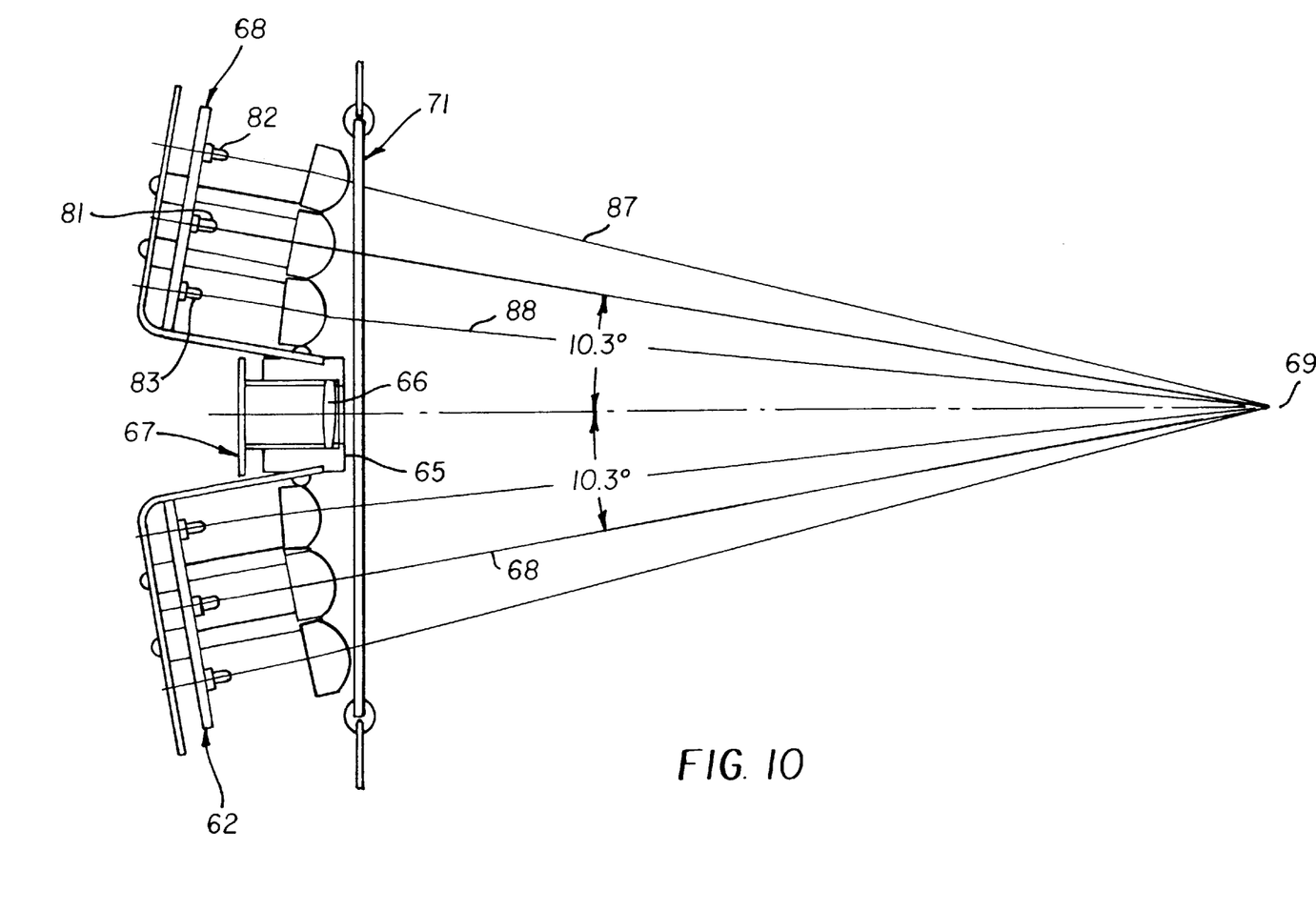
FIG. 10 illustrates an embodiment wherein a lens portion is angularly disposed relative to a respective row of light emitting sources.

FIG. 9 is a block diagram of the signal handling features of a sorter system such as is shown in the mechanical schematic representations of FIGS. 1 and 7. Moving from left to right in the block diagram, the sorter comprises the following sections: sensor assembly 91, signal processing 92, signal analysis 93, rejector logic 94 and rejector mechanism 95. The features shown in the exemplary representations of FIGS. 1, 7 and 9 typically comprise a subsystem of a larger facility, which may be a more comprehensive sorter arrangement, and may suitably further include for example a roller or other conveyor, a wiper system, a clean-in-place system and a control feature, the latter preferably including a control panel or other control arrangement. Such systems may also include features for data capture and output, as well as data analysis to provide information indicative of system performance.

In the system of FIG. 9, image information is sensed from returned light picked up by a sensing assembly 91 such as that indicated in FIG. 4, reference 55, or FIG. 5, references 66 and 67, the returned light providing a measure of product quality. As already described, defective product is deflected to a bin or receptor for reject product by rotation of fingers 96 upwardly and to the right as shown in FIG. 9, from a clear or normally open disposition in which they fulfill no deflecting function and the good product continues its freefall path of movement into a bin or receptor. The deflector units may obviously also be located to either side of the product flow. If transferred to the right, in the views of FIGS. 1, 7 and 9, deflector action is achieved by clockwise rotation of the fingers rather than clockwise. The inspection device of the invention may be adapted to detect defective product and/or the presence of extraneous matter. In the case of fruit or vegetable products, defective product may include unripe or over-ripe product, or product having other specified defects such as scarring, black mould, or other surface imperfections. Extraneous matter may include dirt, leaves and other unwanted vegetable material. In addition to detecting the presence of defects and extraneous matter, the system may also be adapted to provide for distinguishing between particular levels of defect, for example assessing whether or not a particular degree of scarring or mould justifies rejection or acceptance.

In the block diagram of FIG. 9, the signal processing stage 92 amplifies the signals indicative of light levels provided by the sensor 91, to provide numeric data in analog or digital form derived from the conversion of voltage values. In the signal analysis stage 93, the information derived from the returned or reflected light is analysed for information about the physical attributes revealed by the monitoring operation, so that desired characteristics of the object to be monitored are established for use in operational decisions or outputs to be based on this information. The characteristics in question may include the presence of mould, scars, stem and blossom end, and other imperfections, as well as an assessment of the level of severity of these characteristics, and optionally also product size. From this information, a decision may be established as to whether or not a particular product is acceptable or should be rejected.

Output signals from the analysis stage 93 drive reject logic 94 to establish which of the fingers 96 of the reject mechanism 95 are required to be activated, and for what period, to direct an identified defective object into the reject region away from the flow of good product. The particular fingers 96 to be displaced are located at a disposition along the transverse extent of the finger bank corresponding to the path of travel of the particular defective object identified on the width of the path of product advance defined by the conveyor.

FIG. 9 also shows in dotted outline a number of additional optional signal processing logic modules 92a, b, c and d which may provide optional further inputs to the analysis stage 93. Information relating to product quality or characteristics derived from other sensing or monitoring techniques may thus be associated with the light signals from the present system, to enable the apparatus to establish whether or not a product should be rejected on a combined criterion involving two or more conditions or product assessments.

In addition to the finger drive output provided by the arrangement of FIG. 9, the system may also provide outputs to further aspects of a product handling system, for example for control of downstream processing steps, and in particular for data assessment, to provide statistics and other relevant data pertinent to production. Further features 94a and 94b of the block diagram, shown in dotted outline, thus indicate in generalised form, means for appraising the information derived from the inspection operations of the present invention, and for the preparation of reports and for the furnishing of output information for downstream process control.

We claim:

1. An optical inspection system for edible natural products comprising:

an inspection region through which said products pass;

at least one means for directing light onto said products during their passage through said inspection region; and means for detecting light returned from said products;

wherein said at least one light directing means comprises an optical system for focusing light substantially at a specified target region within said inspection region through which target region said products travel during their said passage through said inspection region;

said at least one light directing means and said returned light detecting means are separated from said inspection region by light-transmitting but product-impermeable means wherein there is a spacing between the target region and the light-transmitting but product-impermeable means;

said at least one light directing means comprises a plurality of rows of light emitting sources, each row of said plurality of rows comprising a multiplicity of said light emitting sources;

said optical system comprises a lens system for said focusing of light emanating from said light emitting sources substantially at said target region;

said lens system comprises a plurality of lens system portions, a respective lens system portion corresponding to each of said plurality of rows of light emitting sources; and each of said plurality of rows of light emitting sources is positioned relative to the respective lens system portion corresponding therewith so that light from each row of said plurality of rows focuses substantially at said target region at said spacing from said light-transmitting but product impermeable means; and wherein at least one of said lens portions is angularly disposed relative to the respective row of light emitting sources associated with said at least one lens portion so as to focus light onto said target region.

2. An inspection system according to claim 1, wherein said plurality of lens system portions comprises a plurality of cylindrical lens portions defined by portions of a single unitary lens structure.

3. An inspection system according to claim 1, wherein one of said rows of light emitting sources comprises light sources of at least one first wavelength and another of said rows comprises light sources of at least one second wavelength, said at least one second wavelength being different from said at least one first wavelength, said means for detecting returned light comprises an axial array of sensors located in substantial proximity to said plurality of rows of light emitting sources, and said at least one light directing means is located so that the central optical axis of said at least one light directing means is aligned to focus on said target region.

4. An inspection system according to claim 1, comprising a plurality of said light directing means, wherein each of said plurality of light directing means comprises at least three rows of light emitting sources, a central row comprising light sources for emitting light of at least one first wavelength being flanked by at least two rows comprising light sources for emitting light of at least one second wavelength, said at least one second wavelength being different from said at least one first wavelength, at least one row comprising light sources of said at least one second wavelength being located to each side of said central row, said means for detecting returned light being located substantially centrally between two of said plurality of said light directing means, and wherein said means for detecting returned light comprising an elongate axial array of sensors mounted on an optic bar, and said two of said plurality of said light directing means are mounted one to each side of said optic bar so that the central optical axis of each of said two of said plurality of said light directing means is aligned to focus on said target region.

5. A system according to claim 1 wherein said spacing between said target region and said light-transmitting but product-impermeable means is 290 mm.

6. An optical inspection system for edible natural products comprising:
an inspection region through which said products pass;
at least one means for directing light onto said products during their passage through said inspection region; and
means for detecting light returned from said products;
wherein said at least one light directing means comprises an optical system for focusing light substantially at a specified target region within said inspection region through which target region said products travel during their said passage through said inspection region;
said at least one light directing means and said returned light detecting means are separated from said inspection region by light-transmitting but product-impermeable means wherein there is a spacing between the target region and the light-transmitting but product-impermeable means;
said at least one light directing means comprises a plurality of rows of light emitting sources, each row of said plurality of rows comprising a multiplicity of said light emitting sources;
said optical system comprises a lens system for said focusing of light emanating from said light emitting sources substantially at said target region;
said lens system comprises a plurality of lens system portions, a respective lens system portion corresponding to each of said plurality of rows of light emitting sources; and
each of said plurality of rows of light emitting sources is positioned relative to the respective lens system portion corresponding therewith so that light from each row of said plurality of rows focuses substantially at said target region at said spacing from said light-transmitting but product impermeable means; and
wherein said plurality of lens system portions comprises a plurality of individual cylindrical lens portions defining a lens assembly in which the individual cylindrical lens portions are located substantially in edge contact with one another.

7. An inspection system according to claim 6, wherein one of said rows of light emitting sources comprises light sources of at least one first wavelength and another of said rows comprises light sources of at least one second wavelength, said at least one second wavelength being different from said at least one first wavelength, said means for detecting returned light comprises an axial array of sensors located in substantial proximity to said plurality of rows of light emitting sources, and said at least one light directing means is located so that the central optical axis of said at least one light directing means is aligned to focus on said target region.

8. An inspection system according to claim 6, comprising a plurality of said light directing means, wherein each of said plurality of light directing means comprises at least three rows of light emitting sources, a central row comprising light sources for emitting light of at least one first wavelength being flanked by at least two rows comprising light sources for emitting light of at least one second wavelength, said at least one second wavelength being different from said at least one first wavelength, at least one row comprising light sources of said at least one second wavelength being located to each side of said central row, said means for detecting returned light being located substantially centrally between two of said plurality of said light directing means, and wherein said means for detecting returned light comprising an elongate axial array of sensors mounted on an optic bar, and said two of said plurality of said light directing means are mounted one to each side of said optic bar so that the central optical axis of each of said two of said plurality of said light directing means is aligned to focus on said target region.

9. A system according to claim 6, wherein said spacing between said target region and said light-transmitting but product-impermeable means is 290 mm.

10. An optical inspection system for edible natural products comprising:
an inspection region through which said products pass;
at least one means for directing light onto said products during their passage through said inspection region, and
means for detecting light returned from said products;
wherein said at least one light directing means comprises an optical system for focusing light substantially at a specified target region within said inspection region through which target region said products travel during their said passage through said inspection region;
said at least one light directing means and said returned light detecting means are separated from said inspection region by light-transmitting but product-impermeable means wherein there is a spacing between the target region and the light-transmitting but product-impermeable means;
said at least one light directing means comprises a plurality of rows of light emitting sources, each row of said plurality of rows comprising a multiplicity of said light emitting sources,
said optical system comprises a lens system for said focusing of light emanating from said light emitting sources substantially at said target region,
said lens system comprises a plurality of lens system portions, a respective lens system portion corresponding to each of said plurality of rows of light emitting sources;
each of said plurality of rows of light emitting sources is positioned relative to the respective lens system portion corresponding therewith so that light from each row of said plurality of rows focuses substantially at said target region at said spacing from said light-transmitting but product impermeable means; and
wherein at least one of said rows of light emitting sources is laterally displaced relative to an optical axis of the respective lens portion associated with said at least one row.

11. An inspection system according to claim 10, wherein said plurality of lens system portions comprises a plurality of cylindrical lens portions defined by portions of a single unitary lens structure.

12. An inspection system according to claim 10, wherein one of said rows of light emitting sources comprises light sources of at least one first wavelength and another of said rows comprises light sources of at least one second wavelength, said at least one second wavelength being different from said at least one first wavelength, said means for detecting returned light comprises an axial array of sensors located in substantial proximity to said plurality of rows of light emitting sources, and said at least one light directing means is located so that the central optical axis of said at least one light directing means is aligned to focus on said target region.

13. An inspection system according to claim 10, comprising a plurality of said light directing means, wherein each of said plurality of light directing means comprises at least three rows of light emitting sources, a central row comprising light sources for emitting light of at least one first wavelength being flanked by at least two rows comprising light sources for emitting light of at least one second wavelength, said at least one second wavelength being different from said at least one first wavelength, at least one row comprising light sources of said at least one second wavelength being located to each side of said central row, said means for detecting returned light being located substantially centrally between two of said plurality of said light directing means, said means for detecting returned light comprising an elongate axial array of sensors mounted on an optic bar, and said two of said plurality of said light directing means being mounted one to each side of said optical so that the central optical axis of each of said two of said plurality of said light directing means is aligned to focus on said target region.

14. A system according to claim 10, wherein said spacing between said target region and said light-transmitting but product-impermeable means is about 290 mm.

15. An optical inspection system for edible natural products comprising:

an inspection region through which said products pass;

at least one means for directing light onto said products during their passage through said inspection region; and means for detecting light returned from said products;

wherein said at least one light directing means comprises an optical system for focusing light substantially at a specified target region within said inspection region through which target region said products travel during their said passage through said inspection region;

said at least one light directing means and said returned light detecting means are separated from said inspection region by light-transmitting but product-impermeable means wherein there is a spacing between the target region and the light-transmitting but product-impermeable means;

said at least one light directing means comprises a plurality of rows of light emitting sources, each row of said plurality of rows comprising a multiplicity of said light emitting sources;

said optical system comprises a lens system for said focusing of light emanating from said light emitting sources substantially at said target region;

said lens system comprises a plurality of lens system portions, a respective lens system portion corresponding to each of said plurality of rows of light emitting sources; and each of said plurality of rows of light emitting sources is positioned relative to the respective lens system portion corresponding therewith so that light from each row of said plurality of rows focuses substantially at said target region at said spacing from said light-transmitting but product impermeable means; and wherein at least one of said lens portions is angularly disposed relative to the respective row of light emitting sources associated with said at least one lens portion so as to focus light onto said target region.

16. An inspection system according to claim 15, wherein one of said rows of light emitting sources comprises light sources of at least one first wavelength and another of said rows comprises light sources of at least one second wavelength, said at least one second wavelength being different from said at least one first wavelength, said means for detecting re turned light comprises an axial array of sensors located in substantial proximity to said plurality of rows of light emitting sources, and said at least one light directing means is located so that the central optical axis of said at least one light directing means is aligned to focus on said target region.

17. An inspection system according to claim 15, comprising a plurality of said light directing means, wherein each of said plurality of light directing means comprises at least three rows of light emitting sources, a central row comprising light sources for emitting light of at least one first wavelength being flanked by at least two rows comprising light sources for emitting light of at least one second wavelength, said at least one second wavelength being different from said at least one first wavelength, at least one row comprising light sources of said at least one second wavelength being located to each side of said central row, said means for detecting returned light being located substantially centrally between two of said plurality of said light directing means, and wherein said means for detecting returned light comprising an elongate axial array of sensors mounted on an optic bar, and said two of said plurality of said light directing means are mounted one to each side of said optic bar so that the central optical axis of each of said two of said plurality of said light directing means is aligned to focus on said target region.

18. A system according to claim 15, wherein said spacing between said target region and said light-transmitting but product-impermeable means is 290 mm.

19. An optical inspection system for edible natural products comprising:

(a) an inspection region through which said products pass, (b) at least one means for directing light onto said products during their passage through said inspection region, and (c) means for detecting light returned from said products, wherein (i) said at least one light directing means comprises an optical system for focussing light substantially at a specified target region within said inspection region through which target region said products travel during their said passage through said inspection region, (ii) said at least one light directing means and said returned light detecting means are separated from said inspection region by light-transmitting but product-impermeable means, (iii) said at least one light directing means is disposed so that the spacing between said target region and said light-transmitting but product-impermeable means is sufficient to substantially minimize build-up of unwanted matter on a surface of said light-transmitting but product-impermeable means directed towards said target region, (iv) said at least one light directing means comprises a plurality of rows of light emitting sources, each row of said plurality of rows comprising a multiplicity of said light emitting sources, (v) said optical system comprises a lens system for said focussing of light emanating from said light emitting sources substantially at said target region, (vi) said lens system comprises a plurality of lens system portions, a respective lens system portion corresponding to each of said plurality of rows of light emitting sources, (vii) at least one row of said plurality of rows of light emitting sources is positioned relative to the respective lens system portion associated with said at least one row so that light from each row of said plurality of rows focusses substantially at said target region at said spacing from said light-transmitting but product impermeable means, and (viii) said light emitting sources are arranged in a plurality of substantially parallel rows, and each lens system portion comprises at least one substantially cylindrical lens portion extending generally parallel to the respective row of light emitting sources.

* * * * *